(12) United States Patent
Ciccaglione et al.

(10) Patent No.: US 11,696,611 B2
(45) Date of Patent: *Jul. 11, 2023

(54) HELMET-BASED SYSTEM FOR IMPROVED PRACTICE EFFICIENCY AND ATHLETE SAFETY

(71) Applicant: Sarah Nicole Ciccaglione, Farmington, CT (US)

(72) Inventors: Sarah Nicole Ciccaglione, Farmington, CT (US); Ross Evans Moseley, Norman, OK (US); Austin Price Graham, Allen, TX (US); Sebastian Andrew Columba Tippett, St. Paul, MN (US)

(73) Assignee: Sarah Nicole Ciccaglione, Farmington, CT (US)

( * ) Notice: Subject to any disclaimer, the term of this patent is extended or adjusted under 35 U.S.C. 154(b) by 49 days.

This patent is subject to a terminal disclaimer.

(21) Appl. No.: 17/458,126

(22) Filed: Aug. 26, 2021

(65) Prior Publication Data
US 2022/0047029 A1 Feb. 17, 2022

Related U.S. Application Data

(63) Continuation of application No. 16/864,539, filed on May 1, 2020, now Pat. No. 11,116,271, which is a
(Continued)

(51) Int. Cl.
*A42B 3/04* (2006.01)
*A42B 3/20* (2006.01)
(Continued)

(52) U.S. Cl.
CPC ............. *A42B 3/046* (2013.01); *A42B 3/042* (2013.01); *A42B 3/185* (2013.01); *A42B 3/20* (2013.01);
(Continued)

(58) Field of Classification Search
CPC .. G06K 9/00664–00704; G06F 3/0481; G06F 3/04817; G06F 9/4443;
(Continued)

(56) References Cited

U.S. PATENT DOCUMENTS 7,612,686 B1  11/2009  Bustamante et al.
8,620,600 B2  12/2013  Vock et al.
(Continued)

OTHER PUBLICATIONS

International Search Report and Written Opinion, dated Oct. 23, 2019, for International Application No. PCT/US19/040947.
(Continued)

*Primary Examiner* — Todd Buttram
(74) *Attorney, Agent, or Firm* — Build IP, LLC; Robert V. Donahoe (57) ABSTRACT

A system is provided for use by athletes and their coaches during practice. The system includes an electronic system configured for inclusion in a helmet. The electronic system includes a transparent display screen coupled to the helmet, a processor coupled to the transparent display screen, a camera coupled to the processor and a first wireless transceiver coupled to the processor. The system also includes a handheld processing device. The handheld processing device includes a second wireless transceiver configured to communicate video content with the first wireless transceiver, an interactive display screen configured to display the first video and a video editing application configured to edit the first video to generate a second video including a simulated player technique superimposed in the first video. The second video is communicated from the handheld processing device to the electronic system for display to the athlete via the transparent display screen.

24 Claims, 5 Drawing Sheets

Related U.S. Application Data continuation of application No. 16/034,038, filed on Jul. 12, 2018, now Pat. No. 10,834,986.

(60) Provisional application No. 62/842,121, filed on May 2, 2019.

(51) Int. Cl.
| | |
|---|---|
| *A42B 3/22* | (2006.01) |
| *A42B 3/18* | (2006.01) |
| *G02B 27/01* | (2006.01) |
| *A61F 9/02* | (2006.01) |
| *A61F 9/04* | (2006.01) |
| *A62B 18/04* | (2006.01) |
| *A62B 18/08* | (2006.01) |
| *G01C 21/36* | (2006.01) |
| *G06T 19/00* | (2011.01) |
| *G06F 3/16* | (2006.01) |
| *A42B 3/08* | (2006.01) |

(52) U.S. Cl.
CPC .............. *A42B 3/22* (2013.01); *A61F 9/02* (2013.01); *A61F 9/045* (2013.01); *A62B 18/04* (2013.01); *A62B 18/08* (2013.01); *G01C 21/365* (2013.01); *G01C 21/3697* (2013.01); *G02B 27/0172* (2013.01); *G06T 19/006* (2013.01); *A42B 3/08* (2013.01); *G02B 2027/0138* (2013.01); *G02B 2027/0141* (2013.01); *G06F 3/167* (2013.01)

(58) Field of Classification Search
CPC .. G06F 3/04847; G06F 11/3664; G06F 3/011; G06F 3/012; G06F 3/0304; G06T 19/00; G06T 17/00; G06T 19/006; G06T 2215/16; H04N 5/272; H04N 2201/3245; A63F 13/10
See application file for complete search history.

(56) References Cited

U.S. PATENT DOCUMENTS

| | | | |
|---|---|---|---|
| 8,964,298 B2 | 2/2015 | Haddick et al. | |
| 9,069,166 B2 | 6/2015 | Abdollahi et al. | |
| 9,354,446 B2 | 5/2016 | Abdollahi et al. | |
| 9,354,447 B2 | 5/2016 | Abdollahi et al. | |
| 9,898,912 B1 | 2/2018 | Jordan, II et al. | |
| 10,834,986 B2 | 11/2020 | Ciccaglione et al. | |
| 11,116,271 B2* | 9/2021 | Ciccaglione | A42B 3/20 |
| 2006/0220649 A1 | 10/2006 | Martinez et al. | |
| 2007/0086624 A1* | 4/2007 | Breed | B60R 21/01552 382/104 |
| 2010/0095439 A1 | 4/2010 | Nolan et al. | |
| 2012/0235884 A1* | 9/2012 | Miller | G06F 3/013 345/8 |
| 2012/0262297 A1 | 10/2012 | Poon | |
| 2015/0355709 A1* | 12/2015 | Lee | G06F 3/0346 345/156 |
| 2016/0078278 A1* | 3/2016 | Moore | G02B 27/017 345/8 |
| 2016/0184703 A1* | 6/2016 | Brav | A63F 13/213 463/30 |
| 2016/0220167 A1 | 8/2016 | Allen et al. | |
| 2017/0039480 A1* | 2/2017 | Bitran | A61B 5/01 |
| 2017/0072283 A1* | 3/2017 | Davisson | H04N 5/272 |
| 2018/0050171 A1 | 2/2018 | Tabert et al. | |
| 2018/0129276 A1* | 5/2018 | Nguyen | G06F 3/016 |
| 2019/0011556 A1* | 1/2019 | Pacala | G01S 7/4817 |
| 2019/0064344 A1* | 2/2019 | Turner | G08B 25/016 |
| 2020/0015536 A1* | 1/2020 | Ciccaglione | A61F 9/029 |
| 2020/0128899 A1* | 4/2020 | Greenblatt | A42B 3/046 |
| 2020/0329801 A1* | 10/2020 | Ciccaglione | G01C 21/3697 |
| 2022/0047029 A1* | 2/2022 | Ciccaglione | A42B 3/22 |

OTHER PUBLICATIONS

Yang, Halla, NFL Punt Analytics Proposal, Feb. 2, 2019, retrieved May 1, 2020, https://www.kaggle.com/hallayang/nfl-punt-analytics-proposal.

Bogage, Jacob, "The future of football equipment? Measuring a hit's impact on the brain, not just the helmet," Washington Post, Jun. 2, 2017, retrieved May 1, 2020, https://www.washingtonpost.com/sports/highschools/the-future-of-football-equipment-measuring-a-hits-impact-on-the-brain-not-just-the-helmet/2017/06/02/d6dd0cb8-47b0-11e7-98cd-af64b4fe2dfc_story.html.

* cited by examiner

HELMET-BASED SYSTEM FOR IMPROVED PRACTICE EFFICIENCY AND ATHLETE SAFETY

BACKGROUND OF INVENTION

1. Field of Invention

This invention relates generally to apparatus, systems and methods including a helmet equipped with sensors worn by athletes in sports in which athletes are routinely subject to impacts. More specifically, at least one embodiment, relates to apparatus, systems and methods providing a helmet-based system for improving practice efficiency and athlete safety.

2. Discussion of Related Art

Athletes often compete in sports that require that a helmet be worn while participating in the sport to protect the athlete's head from violent impacts that occur. However, concussions remain a common occurrence in sports, for example, football, even though a helmet is required equipment for participants in the sport. Over time, the medical industry has come to recognize and better understand the long term harm caused by repeated head injuries, referred to as chronic traumatic encephalopathy (CTE). This awareness has led to an implementation of formal concussion protocols to prevent the participation of an athlete with current symptoms of a concussion. The leagues and other governing bodies for these sports are also working to design improved protective equipment to eliminate or reduce the occurrence of concussions and related head injuries. However, none of these approaches provide the information necessary to monitor and analyze the cumulative effect of repeated impacts to prevent the occurrence of a concussion, prevent the lasting damage caused by repeated impacts that may or may not be concussive or to rapidly identify an athlete suffering from a concussive impact.

Today, coaching staffs and athletes have access to a huge amount of information, for example, digital information such as video, audio and graphics content. The information can include playbooks as well as video recorded at practice and at competitions as a few examples. However, the tools for the analysis, playback and sharing of the information have not kept pace. As a result, this wealth of information is not available in a substantially real time basis to teach athletes and improve their performance. Further, when coaching staffs attempt to use the information it can actually reduce the efficiency in the practices.

SUMMARY OF INVENTION

Therefore, there is a need for helmet-based safety systems that collect and analyze data for an athlete to provide a predictive approach that mitigates the risk of, or entirely prevents, concussions. There is also a need for apparatus, systems and methods to provide safety systems including sensors integrated into an otherwise conventional protective headgear, for example, a football helmet. According to some embodiments, sensor data regarding current impact(s) is analyzed in substantially real-time with information concerning an athlete's impact history, concussion history and overall medical history to determine whether the athlete's current participation should be limited or stopped as either a preventive measure or because the athlete has likely suffered a concussion. In further embodiments, wireless communication allows data recorded by a system included in the helmet to be communicated to coaching staff or medical staff for evaluation in substantially real time. In one embodiment, alerts or notifications can be generated and communicated to athlete, coach or medical staff.

In some further embodiments, the helmet-based system includes a heads-up-display ("HUD") that allows a communication and sharing of video and other visual content with the display included in the helmet. In some embodiments, the shared information can be employed to improve the effectiveness and efficiency of practices, for example, to more rapidly install game plans and improve the performance of athletes. In further embodiments, the HUD provides information used to increase the safety of the athletes. In other embodiments, the information is displayed in a user device in possession of the coaching staff and/or medical staff. According to this embodiment, the information can include information to improve the efficiency of practices and/or athlete safety. According to one embodiment, the version of the helmet that includes the HUD is only employed in practice-helmets and a HUD is not included in helmets used in competition.

In one aspect, a system is provided for use by athletes and their coaches during practice. The system includes a helmet-based electronic system, a handheld processing device and an artificial intelligence engine configured to determine at least one threshold concerning a plurality of physiological states. According to one embodiment, the helmet-based electronic system includes a transparent display screen coupled to a helmet, the transparent display screen configured to display information to the user in a video format and a graphical format, a processor coupled to the transparent display screen, a sensing system configured to sense a plurality of physiological states of the athlete when participating in a practice-activity and a first wireless transceiver coupled to the processor, the first wireless transceiver configured to communicate information concerning the plurality of physiological states. According to a further embodiment, the handheld processing device includes a second wireless transceiver configured to communicate with the first wireless transceiver and an interactive display screen configured to display the information concerning the plurality of physiological states received from the first wireless transceiver for review by a member of a coaching staff. A first notification is automatically generated by the handheld processing device and displayed in the interactive display screen when a processing of the information concerning the plurality of physiological states results in a value that exceeds the threshold. A second notification is communicated to the helmet-based electronic system for display on the transparent display screen, the second notification providing instructions for the athlete to modify the practice-activity.

According to another aspect, a system is provided for use by athletes and their coaches during practice. According to some embodiments, the system includes an electronic system configured for inclusion in a helmet and a handheld processing device. The electronic system includes a transparent display screen coupled to the helmet, the transparent display screen configured to display video content, a processor coupled to the transparent display screen, a camera coupled to the processor and a first wireless transceiver coupled to the processor. The first wireless transceiver is configured for a communication of at least the video content and the camera is configured to record a first video from the athlete's point of view when participating in a practice activity when wearing a helmet including the helmet-based electronic system. The handheld processing device includes a second wireless transceiver configured to communicate the video content with the first wireless transceiver, an interactive display screen configured to display the first video and a video editing application configured to edit the first video to generate a second video including a simulated player technique superimposed in the first video. According to one embodiment, the second video is communicated from the handheld processing device to the helmet-based electronic system for display to the athlete via the transparent display screen.

According to still another aspect, a system is provided for use by athletes and their coaches during practice. According to some embodiments, the system includes a helmet-based electronic system and a handheld processing device. The helmet-based electronic system includes a transparent display screen coupled to the helmet, a processor coupled to the transparent display screen, at least one sensor coupled to the processor and configured to provide information concerning a performance of an athlete wearing a helmet including the helmet-based electronic system when participating in a practice-activity and a first wireless transceiver coupled to the processor, the first wireless transceiver configured to communicate the information concerning the performance of the athlete. The transparent display screen is configured to display information to the user in a video format and a graphical format. The handheld processing device includes a second wireless transceiver configured to communicate with the first wireless transceiver and an interactive display screen configured to both display the information concerning the performance of the athlete received from the helmet-based electronic system for review by a member of a coaching staff and to receive an entry of at least one action from the member of the coaching staff, the at least one action concerning a change to the practice-activity. According to further embodiments, the information concerning the performance of the athlete concerns at least one of a position of the athlete on a playing field during the practice activity, a speed of the athlete during the practice activity and a reaction time of the athlete during the practice activity. Further, the at least one action is communicated to the helmet-based electronic system via the second wireless transceiver for display to the athlete wearing the helmet. The at least one sensor provides information concerning the performance of the athlete after taking the at least one action and participating in the practice-activity again. The information concerning the performance of the athlete after taking the at least one action and participating in the practice-activity again is communicated from the helmet-based system to the handheld processing device for review by the member of the coaching staff.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Figure 1:
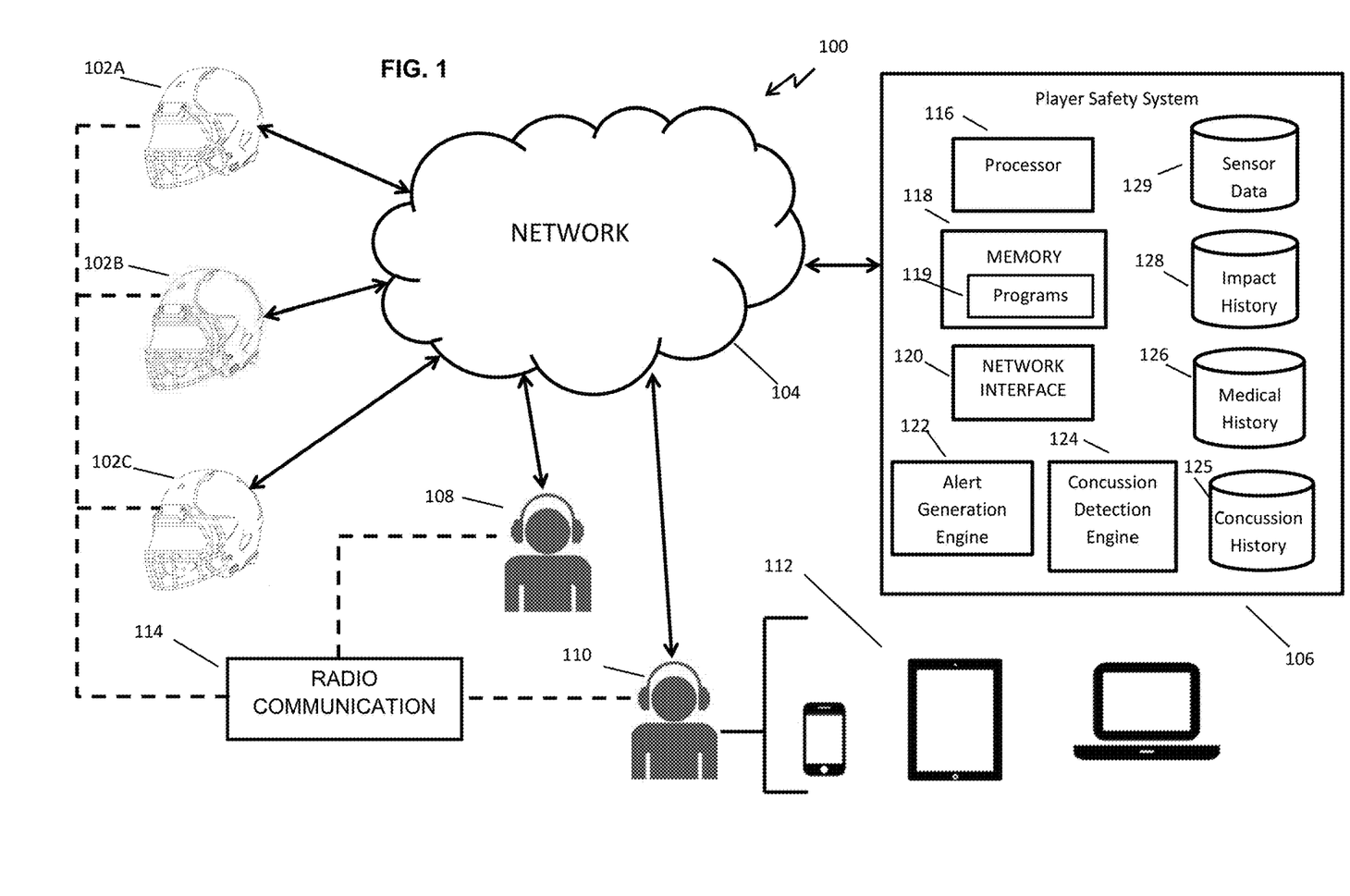
FIG. 1 illustrates a system including a network operating environment for a helmet-based safety system in accordance with one embodiment.

Referring now to FIG. 1, a network operating environment for a helmet-based safety system 100 is illustrated in accordance with various embodiments. According to the illustrated embodiment, the system 100 includes a plurality of helmets 102A-C worn by athletes, a network 104, resources 106, coaching staff 108, medical staff 110 and a plurality of user devices 112. Optionally, the system 100 can include a radio communication system 114. In various embodiments, the system 100 is employed to collect and analyze sensor data concerning impacts as recorded by systems included in the plurality of helmets 102A-C as described in greater detail below.

In various embodiments, each of the plurality of helmets 102A-102C includes a system, for example, an electronic system including an inertial sensing system, respectively. As is described in greater detail below, the electronic system that is integral to the helmet detects and measures impacts that occur when the helmet is being worn by the athlete. Depending on the embodiment, the electronic system can also operate a heads-up-display (HUD) included in the helmet.

In general, the network 104 can include either or both of local-area networks (LANs), wide area networks (WANs), wireless communication, wired communication and may include the Internet. According to a further embodiment, the network 104 provides access to one or more remote devices, servers, application resource management and/or data storage systems, for example, the resources 106. In general, the system 100 provides for communication of the illustrated components with one another and/or with any of the other resources and devices coupled to the network 104. For example, the network 104 can allow communication between any of the athletes using the plurality of helmets 102A-C, the coaching staff 108 and the medical staff 110 employing a selected one of the plurality of user devices 112, respectively, and one another or with the resources 106. Communication can occur using any of Wi-Fi networks, Bluetooth communication, cellular networks, satellite communication, and peer-to-peer networks available either alone or in combination with one another via the network 104. Depending on the embodiment, the network 104 may be any type and/or form of network known to those of ordinary skill in the art capable of supporting the operations described herein. Thus, other communication protocols and topologies can also be implemented in accordance with various embodiments.

Further, in the illustrated embodiment, the radio communication system 114 can be included to allow communication between athletes, coaches and staff without reliance on any equipment such as cellular, satellite or other communications hardware that is geographically remote from the users. According to alternate embodiments, the radio communication system 114 can be replaced by other forms of communication, for example, cellular communication or wireless peer to peer communication.

In various embodiments, the resources 106 provide the interface and tools for storing and analyzing data or other forms of information provided by and/or communicated to any of the plurality of helmets 102A-C, the coaching staff 108 and the medical staff 110. In the illustrated embodiment, the resources 106 include a processor 116, a memory 118, a network interface 120, an alert generation engine 122, a concussion detection engine 124, concussion history data storage 125, medical history data storage 126, impact history data storage 128 and sensor-data data storage 129. The memory 124 includes a plurality of programs 119. Depending on the embodiment, the resources 106 can be hosted on one or more of a variety of computing devices such as a general purpose computer such as a PC, a laptop, a tablet computer, mobile phone, a server or other computing device. According to one embodiment, the resources are distributed across a plurality of computing devices. For example, in some embodiments either or both of the alert generation engine 122 and concussion detection engine 124 are included in one or more of the plurality of football helmets 102A-C and the user devices 112 employed by the coaching and medical staffs. Similarly, one or more of the concussion history data storage 125, the medical history data storage 126, the impact history data storage 128 and the sensor-data data storage 129 can be included in one or more of the plurality of football helmets 102A-C and the user devices 112 employed by the coaching and medical staffs depending on the embodiment.

The network interface 120 is employed for communication, via the network 104, between the resources 106 and other elements connected to the network including the athletes via the plurality of helmets 102A-C, the coaching staff 108 and the medical staff 110.

The memory 118 can store the plurality of programs 119 that when executed by the processor 116 operate to receive, store and manage data included in any of the concussion history data storage 125, the medical history data storage 126, the impact history data storage 128 and the sensor-data data storage 129. According to further embodiments, the plurality of programs 119 operate to process information from any one, any combination or all of the preceding data-stores to generate alerts used to improve athlete safety and to determine whether an athlete has suffered a concussion. In accordance with one embodiment, the alerts and concussion detection algorithms operate in substantially real time.

According to various embodiments, the memory 118 stores programs 119 that when processed by the processor execute algorithms that compare an athlete's current physiological and/or neurological condition with thresholds to determine whether the athlete should continue to participate in a practice or game. The comparisons can result in the initiation of notifications to the athlete, medical staff or coaching staff. Depending on the algorithm, the notifications can trigger because data concerning the athlete's current state: 1) exceeds a threshold value: 2) drops below a threshold value; 3) equals a threshold value; or 4) deviates from within a desired range bounded by threshold values. In some embodiments, a combination of the preceding conditions can trigger an alert or notification. According to some embodiment, an artificial intelligence engine is included in the memory 118. According to these embodiments, machine learning is employed to establish the preceding thresholds that when reached initiate an end, or reduction in an intensity of, the athletic activity being performed by an athlete. In still further embodiments, one or more of the above-described programs are included in a memory included in one or more of the plurality of football helmets 102A-C and the user devices 112 employed by the coaching and medical staffs. When executed by a processor included in the respective device, these programs can execute the machine learning algorithms and parameter processing that compares the athlete's current physiological and/or neurological condition with thresholds to determine whether the athlete should continue to participate in a practice or game.

According to various embodiments, the concussion history data storage 125 stores information that provides details regarding the concussion history for each of the respective athletes monitored by the system 100. This information can include whether an athlete has received a concussion in the past, the date the concussion occurred, the symptoms experienced at the time of the concussion, the duration that symptoms lasted and the nature and type of the symptoms. Other information concerning an athlete's concussion history can be provided in further embodiments.

According to some embodiments, the medical history data storage 126 stores information concerning the overall medical history of the respective athletes monitored by the system 100. This can include information about past ailments, injuries, medical treatment and medical test results to name a few examples. Further, the medical history can provide information about the athlete's mental state as well as their physical state. For example, signs and symptoms of concussion can include headache, nausea, fatigue, confusion or memory problems, sleep disturbances, or mood changes.

The system 100 can also allow substantially real-time communication of audio, video and sensor data to allow the coach staff 108, medical staff 110 and other trainers or staff to monitor an athlete's health during a practice or a game. As some examples, this information can include any of an athlete's hydration level, body temperature, heart rate (including feedback indicative of a possible arrhythmia) and oxygen levels and/or oxygen intake for the athletes. Other physiological data or health-related information can be communicated and processed alone or in combination with the preceding depending on the embodiment. The data can also be stored in the resources 106 for future analysis and/or integration in machine learning employed to establish thresholds for ending, or reducing an intensity of, an athletic activity performed by an athlete.

According to some embodiments, the impact history data storage 128 stores information that provides details regarding the impacts suffered by each of the respective athletes monitored by the system 100. In general, this information is collected when the athlete is wearing one of the plurality of helmets 102A-C, for example, collected by a system included in the plurality of helmets 102A-C. The impact history can catalog dates and times that an athlete's participation in practice or competition results in an impact that exceeds a predetermined threshold (for example, a threshold value that is algorithmically derived), the precise time of each such impact and the magnitude of each such impact, as some examples. According to one embodiment, an artificial intelligence algorithm is employed to establish the threshold value based on a model trained using data from experiences with other athletes where the algorithm processes the individual athlete's impact history to establish the threshold. Additional information can be included in the impact history data storage 128 depending on the embodiment.

According to some embodiments, the sensor-data data storage 129 stores data provided from sensors, for example, accelerometers, gyroscopes or other sensors included in the systems included in each of the plurality of helmets 102A-C. In one embodiment, the sensor-data is processed sensor data. In an alternate embodiment, the sensor data is raw output data from the sensors that is processed by the resources 106, for example, to generate information concerning an athlete's impact history. In each embodiment, the sensor data is communicated from the systems included in each of the respective helmets included in the plurality of helmets 102A-C. According to some embodiments, the sensor data is wirelessly communicated to the resources 106 via the network 104.

Depending on the embodiment, each of the concussion history data storage 125, the medical history data storage 126, the impact history data storage 128 and the sensor-data data storage 129, respectively, can include any of a relational database, object-oriented database, unstructured database, or other database. Further, the concussion history data storage 125, the medical history data storage 126, the impact history data storage 128 and the sensor-data data storage 129 can be included in any aspect of a memory system, such as in RAM, ROM or disc, and may also be separately stored on one or more dedicated data servers included in the resources 106. In addition, the data storage can be organized in a manner different than illustrated in FIG. 1. The various data storage requirements can be modified to combine, modify or eliminate all or a portion of the concussion history data storage 125, the medical history data storage 126, the impact history data storage 128 and the sensor-data data storage 129, respectively, depending on the embodiment.

While the concussion history data storage 125, the medical history data storage 126, the impact history data storage 128 and the sensor-data data storage 129 are identified in FIG. 1, those of ordinary skill in the art will recognize based on the disclosure provided herein that the resources can include storage for other types of data and file-types depending on the embodiment. For example, in some embodiments, the resources 106 include video file storage, for example, MP4 video files. As explained in detail herein, video content can be communicated to the resources 106 for storage and review and also communicated from the resources 106 for playback at the plurality of helmets 102A-C or any of the plurality of user devices 112.

The components included in the resources 106 can be coupled by one or more communication buses or signal lines. The communication buses can be used for the communication of instructions/commands and data between the illustrated components and between the illustrated components and other components included in the resources 106 depending on the embodiment.

The plurality of user devices 112 can include any type of computing device suitable for communicating with the resources 106 via the network 104. Accordingly, the plurality of user devices 112 of can include one or more of a variety of computing devices such as a general purpose computer, for example, a PC, a laptop, a tablet computer, a hand-held computer, a personal digital assistant, a mobile telephone, a camera, a smart phone or a laptop computer.

According to some embodiments, the concussion detection engine 124 operates to process one or more of sensor data, impact history, medical history and concussion history for the respective athletes to determine whether the athlete is at high risk of a concussion or has actually received a concussion. For example, the concussion detection engine 124 may evaluate an impact-magnitude, an impact-direction and/or an impact location relative to one or more respective predetermined threshold(s). Where one of the preceding measures exceeds the threshold, the concussion detection engine can provide that information to one or more elements included in the resources 106, for example, the alert generation engine 122. According to one embodiment, the concussion detection engine operates in substantially real time.

According to some embodiments, the alert generation engine 122 operates to provide notifications to any of the athlete (via the system included in one of the plurality of helmets 102), coaching staff 108 and medical or training staff 110. In one embodiment, the alerts are generated via the processing of any one of or any combination of sensor data, impact history, medical history and concussion history for a selected athlete and then communicated to the helmet worn by the athlete, to a user device 112 in possession of a member(s) of the coaching staff or to a user device 112 in possession of a member(s) of the medical staff. The content of the alerts can vary depending on the embodiment. For example, the alert may include a "red flag" warning to signify to an athlete, coach and/or staff that an athlete likely has a concussion and should immediately be seen by medical staff 110. The alert may also include a "yellow flag" warning to signify that the cumulative impacts received by the athlete place them at risk of a concussion. This alert may be provide to coaches, medical staff or trainers such that the athletes participation can be stopped, scaled back or more closely monitored in an effort to avoid a concussive impact.

Figure 2:
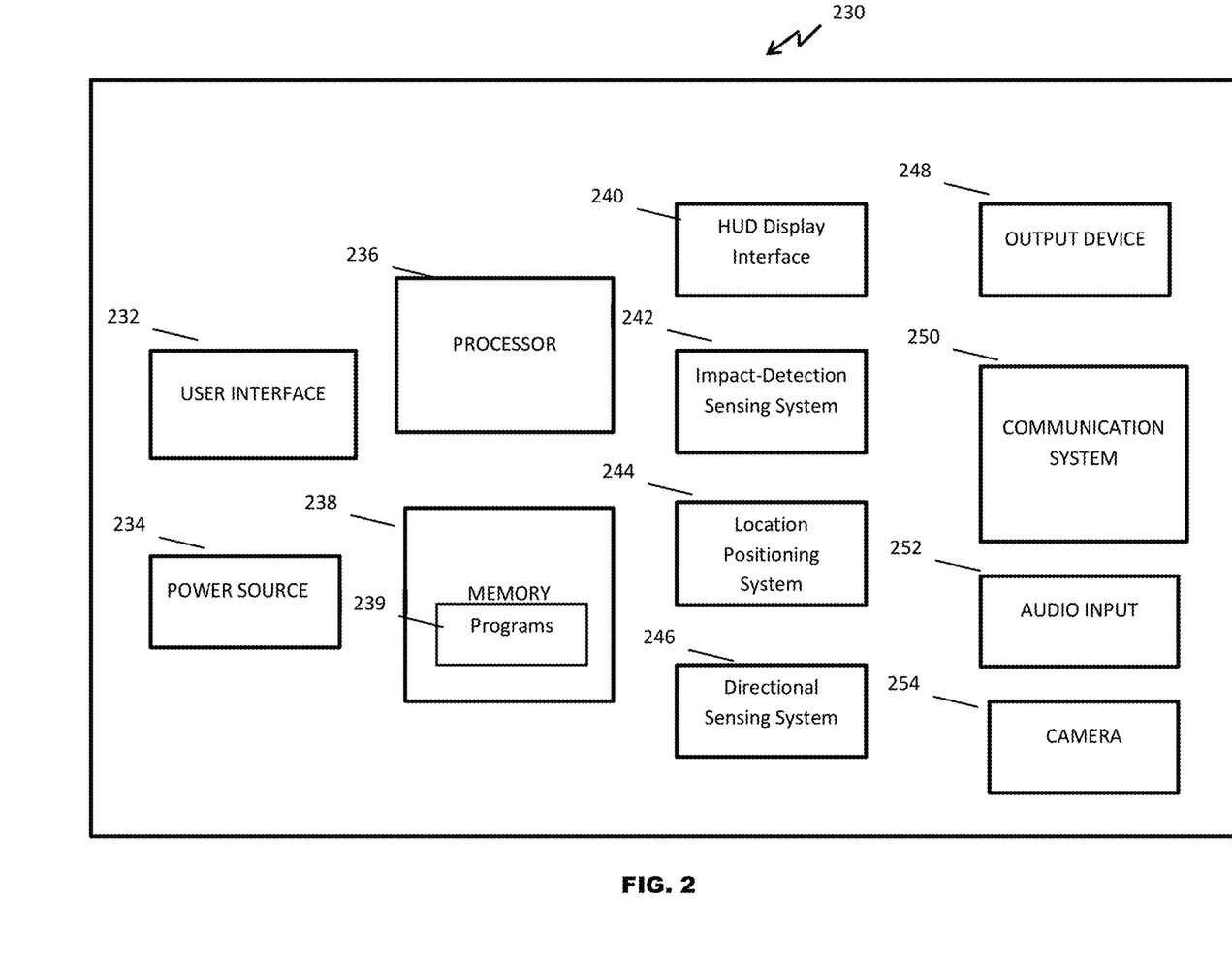
FIG. 2 illustrates a block diagram of an electronic system in accordance with one embodiment.

Referring now to FIG. 2, an electronic apparatus 230 is illustrated in accordance with various embodiments. According to some embodiment, the electronic apparatus 230 includes an electronic device and associated elements that are distributed in an athlete's helmet, for example, the helmet 102 of FIG. 1 or helmet 302 as illustrated in FIGS. 3-6. According to the illustrated embodiment, the electronic apparatus 230 includes a user interface 232, a power source 234, a processor 236, a memory 238 and a HUD display interface 240. One or more sensor systems can be included in the electronic apparatus 230. In the illustrated embodiment, the sensor systems include an impact-detection sensing system 242, a location positioning system 244 and a directional sensing system 246. Further, the electronic apparatus 230 also includes an output device 248, a communication system 250, an audio input 252 and a camera 254.

In general, the user interface 232 allows the user to check the operational status of, to operate and/or configure the electronic apparatus 230. In various embodiments, the user interface 232 can include one or more LEDs or indicating lamps, switches, pushbuttons or voice recognition. According to one embodiment, the user interface 232 includes a GUI. For example, a GUI can be located on an interior or an exterior surface of the helmet 102, respectively depending on the embodiment. According to one embodiment, the user interface is visible in a HUD included in the helmet.

Depending on the embodiment, the processor 236 can be a standalone element, for example, a microprocessor. In another embodiment, the processor 236 is included in microcontroller. In one embodiment, the memory 238 is included in the processor 236. In another embodiment, the memory 238 includes memory internal to the processor 236 and memory external to the processor. Depending on the embodiment, the memory 238 can include RAM, ROM, EEPROM and/or FLASH memory. In various embodiments, the memory 238 is configured to store software instructions 239. Depending on the embodiment, the software instructions 239 can be implemented as individual software programs or modules, or combined with one another in various configurations. Also depending on the embodiment, various functions of the electronic apparatus 230 can be implemented in hardware and/or in software, including in one or more signal processing and/or application specific integrated circuits.

According to some embodiments, the power source 234 includes one or more batteries or other electrical energy storage devices. In one embodiment, the power source 234 includes a rechargeable battery such as a lithium ion battery. According to another embodiment, the power source 234 can include a solar power source such as a photovoltaic panel located on an exterior surface of the helmet 102. The solar power can be employed in combination with a battery power source in some embodiments. According to another embodiment, the power source 234 includes a kinetic-charging system that generates energy from the athlete's motion when the helmet is worn. According to a further embodiment, the power source 234 includes both solar power and kinetic-charging. Where both types of power sources are employed the battery size and weight can be reduced relative to embodiments in which only one of the two power sources are employed. In any of the preceding approaches, the electronic apparatus 230 includes one or more power circuits that connect components included in the apparatus 230 to the power source 234. In some embodiments, the power source 234 provides power to the HUD included in the electronic apparatus 230.

According to various embodiments, the electronic apparatus 230 includes the HUD display interface 240. In one embodiment, the display interface 240 includes a graphics processor (for example, a GPU). In one embodiment, the graphics processor is included in the processor 236. In other embodiments, the display interface 240 including graphics processor is a separate component in the apparatus 230. In further embodiments, the display interface 240 including graphics processor is employed to increase the processing speed in the safety system by performing tasks that would otherwise be performed by the processor 236. According to one embodiment, the HUD display interface 240 includes the graphics processor in a graphics card.

In various embodiments, the impact-detection sensing system 242 includes one or more accelerometers, one or more gyroscopes or both. In accordance with one embodiment, the one or more accelerometers include at least one multi-axis accelerometer, for example, a three axis accelerometer. The measurement range of the accelerometer can be selected based on an expected g force to be measured in the application. Thus, for example, a lower range accelerometer can be used in youth sports where the athletes are below a certain age. A higher range accelerometer can be employed in professional sports where the athletes operate with maximum of speed and force. According to some embodiments, the one or more accelerometers include a multi-axis accelerometer with a plurality of ranges.

In general, the axes of impact are relevant to determining whether an impact is potentially concussive. Further, the fixed location of the helmet relative to the athlete's head lends itself to establishing a known location of an impact. In some embodiments, elements included in the impact-detection sensing system 242 (such as the accelerometer(s) or gyroscope(s)) are placed in a selected orientation to provide improved information concerning the potential concussive effect of various impacts. For example, one or more accelerometers can be oriented to detect acceleration along a selected axis relative to the athlete's physiology. Examples include: 1) an orientation that is selected to provide improved detection of impacts that occur to the crown of the helmet; and 2) an orientation that is selected to provide improved detection of impacts that occur to the back of the helmet. The improved detection can include an increased degree of accuracy for the impact measurements concerning the selected impact location. According to a further embodiment, a gyroscope is oriented to sense angular acceleration about the vertical axis of the user, for example, relative to the neck or spine. For example, in some embodiments, angular position and velocity are measured and employed in an impact-processing algorithm used to improve athlete safety.

In various embodiments, the location positioning system 244 can employ cellular triangulation, RFID, GPS or any of the preceding alone, in combination with one another or in combination with other location positioning technology. In some embodiments, the location positioning system is employed to allow coaches to track an athlete's location on the field. For example, the location of each of a plurality of athletes can be displayed to the coach 108 or medical staff 110 on the plurality of user devices 112 in substantially real-time in accordance with one embodiment. Video tracking via cameras filming practice sessions or competition can also be used to track an athlete's location either alone or in combination with the preceding. The location positioning system 244 can also be employed to measure an athlete's performance according to some embodiments, for example, to determine an athlete's top speed for a given play or the entirety of a practice session or competition. In some embodiments, the location positioning system 244 can be employed to provide location-based services to any of the athletes wearing one of the plurality of helmets 102A-C, the coaches 108 and medical staff 110. In one embodiment, the location-based information is used to customize the information that is available to an athlete depending on their location. For example, depending on whether the athlete is located at a home practice facility or an away practice facility.

According to some embodiments, an RFID-based location positioning system is employed using RFID tags included in the positioning system 244 and RFID tag-sensors strategically located around the playing field or arena to, for example, track a movement of players relative to one another. In some further embodiments, the electronic system 230 includes RFID tag-sensors that detect the location of other players, for example, when in proximity to one another. In a still further embodiment, both RFID tags and RFID tag-sensors are included in the electronic system 230 and are used in combination with RFID tag-sensors located on and around the playing field. The preceding can be provided with various wireless tag readers employed for RFID tag sensing depending on the embodiment. In some further embodiments, RFID tags are also included in the ball used in the athletic activity. For example, an RFID tag can be included in a football. According to these embodiments, the location of the ball is tracked relative to the playing field and/or the location of the players. The object-based tracking can also be employed to analyze the performance of the ball or other sports-object being tracked.

The benefits of the above-described location positioning and tracking embodiments can provide information on athletic performance used to improve practices or actual in-game performance. For example, objective information such as velocities and athlete on-field positioning can be tracked and correlated to actual results.

Depending on the embodiment, the directional sensing system 246 can include a compass, a magnetometer, optical tracking or employ a velocity vector array. In one embodiment, the directional sensing system 246 includes a compass that operates based on information provided by the magnetometer. In some embodiments, the directional sensing system 246 is employed to better improve the results of the processing of the impact data by providing information concerning a relative direction of impact on the athlete.

The electronic apparatus 230 can include a GPS in the location positioning system 244 as described above. According to another embodiment, the GPS is included as a separate component of the electronic apparatus 230. For example, the GPS can include a GPS receiver employed in combination with one or more additional sensing systems included in the directional sensing system 246.

Various types of output devices can be included in the output device 248 and included in the electronic apparatus 230 depending on the embodiment. For example, the output device 248 can include a speaker to provide the user with audio used for communication and/or feedback from the resources 106 such as audible alerts or notifications concerning concussion risks and impacts more generally. In one embodiment, the output device 248 including speaker is employed to play audio associated with video being displayed to the athlete via a HUD. The output device 248 can also include indicating lights such as LEDs. According to further embodiments, the output device 248 includes vibration or other tactile feedback that is delivered to the user when wearing one of the plurality of helmets 102A-C. In other embodiments, all or a portion of the output device 248 are included in a HUD included in the helmet. For example, alerts and notifications can be displayed in the HUD.

Depending on the embodiment, the communication system 250 can include any of Wi-Fi networks, Bluetooth™ communication, cellular networks, satellite communication, and peer-to-peer networks available either alone or in combination with one another. Other communication protocols and topologies can also be implemented in accordance with various embodiments. For example, optical communication can be included in the communication system 250 in some embodiments. According to these embodiments, information is communicated in an optical signal either transmitted from or received by the electronic apparatus 250.

The audio input 252 includes one or more microphones in various embodiments. According to some embodiments, the audio signal received by the audio input 252 is communicated to other users via the communication system 250. In some embodiments, the audio input 252 receives verbal commands from the user, for example, instructions concerning the information to display in the HUD or verbal responses in view of the information already displayed in the HUD.

In various embodiments, the camera 254 includes one or more electronic cameras. Depending on the embodiment, the camera 254 can employ CMOS technology, NMOS technology and CCD technology as a few examples. According to another embodiment, the camera 254 employs quanta image sensing technology. In one embodiment, the electronic apparatus 230 includes multiple cameras, for example, a forward facing camera and a rear facing camera.

According to some embodiments, images and/or video provided by the camera 254 are employed for impact detection. For example, footage recorded by the camera 254 can be processed with object-recognition algorithms to determine a position of a first athlete's body relative to a second athlete's body when the two athletes collide with one another.

Referring now to FIGS. 3-6, a helmet 302 including an electronic apparatus, for example, the electronic apparatus 230, is illustrated in accordance with various embodiments. According to the illustrated embodiment, the helmet is a football helmet. In the illustrated embodiment, the system includes a display 362, electronics compartment 364, a speaker 365, a microphone 366, a first inertial sensing system 367 and a second inertial sensing system 368.

Figure 3:
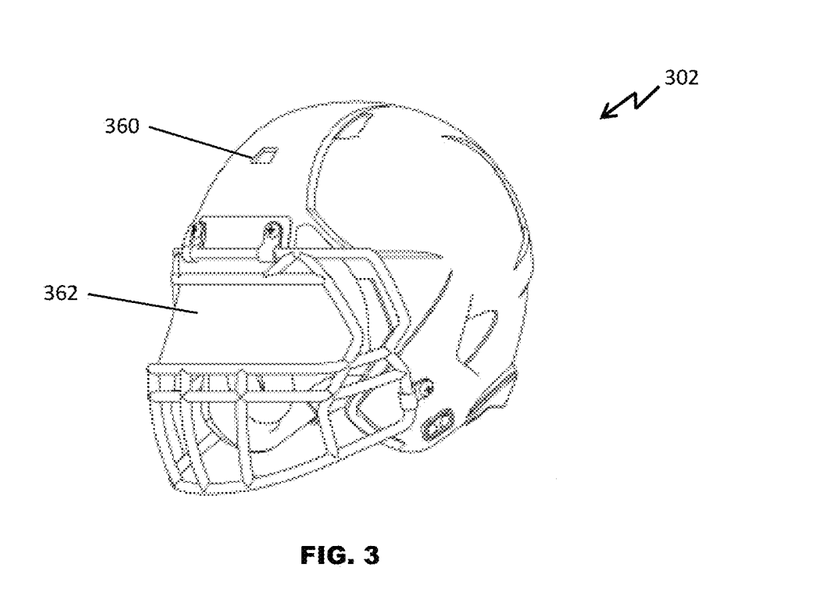
FIG. 3 illustrates an isometric front view of a helmet an integral safety system in accordance with one embodiment.

The display 362 can include different technology depending on the embodiment provided; 1) that the display allows the user to see through the material of the display; 2) that the material is suitable for the display of graphical elements; and 3) that the display has the mechanical strength suitable for repeated impacts typical for the selected application. For example, OLED technology can be employed in some embodiments. According to other embodiments, the display 362 employs one or a combination of LCD technology, light emitting polymer display technology, diffracted layer display technology, waveguide display technology (for example, holographic waveguide technology) and projection heads-up display technology.

The preferred technology can be selected based on the physical flexibility and strength of the material of the display 362. In addition to impact and shock resistance, other design considerations can include the level of transparency of the material and the resolution of the display 362. According to the illustrated embodiment, the display is mounted to the helmet 302 in the location of a visor sometimes employed by athletes. According to these embodiments, the display 362 is provides a helmet-mounted display system, for example, an integral visor-mounted display.

According to various embodiments, the display 362 is transparent. In a further embodiment, a surface covering the display 362 is tinted. According to various embodiments, the display 362 is employed to render a graphical user interface (GUI). In some embodiments, the electronic apparatus 362 includes a speech recognition system that allows the user to interact with the GUI in a hands-free manner. For example, the user can wake the system from a sleep mode with a voice command.

Depending on the embodiment, the display is employed to display video content communicated to the athlete via the coaching staff 108 and/or medical staff 110 via the network 104. The video content can include coaching-content that may or may not address athlete safety. The video content can provide information that the athlete can use to improve their technique to improve their on-field performance. For example, the content may assist the athlete in more quickly understanding an opponent's strategy and technique so the athlete can more quickly place themselves in an improved position to execute their role on the field. The content can also include video that assists an athlete in reducing the risk of a concussion when participating in their sport.

According to the illustrated embodiment, the camera 360 is located in a forward facing position at the front of the helmet. Depending on the embodiment, the cameras can be used to provide footage used in evaluating the potential concussive impact of a particular collision on the athlete wearing the helmet 302. Further, the system 100 allows for communication of the footage from the helmet 302 to other elements included in the system 100, for example, the resources 106, the coaches 108 and the medical staff 110. In addition, as described herein, embodiments of the system can also be employed to provide the athlete with information that can be used to improve the manner in which they compete to either or both of: 1) reduce the likelihood of an impact that causes a concussion; and 2) improve their performance. In accordance with some embodiments, footage recording by the camera is combined with other information provided from the coaching or medical staff and displayed on the display 362. In further embodiments, the camera 360 includes a plurality of cameras, for example, oriented to provide a wider field of view. The preceding can improve practice efficiency by providing multiple views of a play.

Figure 4:
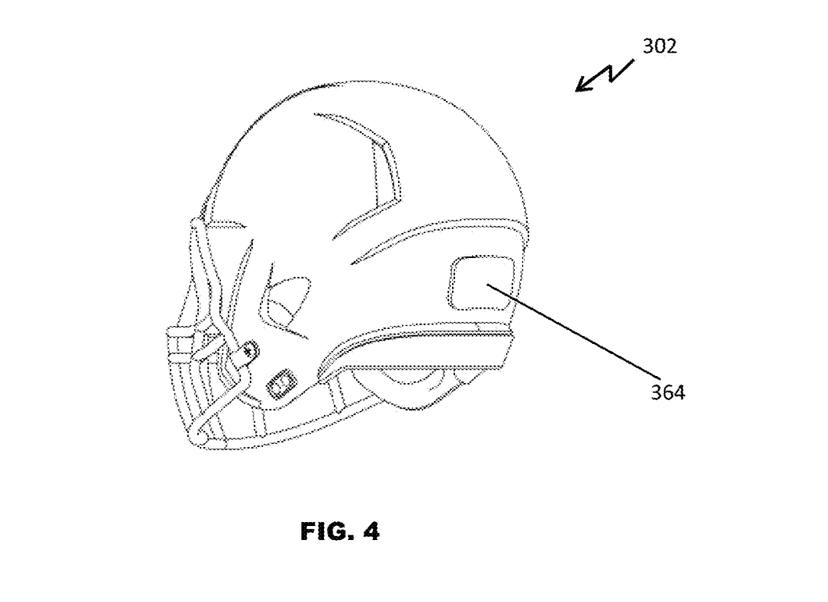
FIG. 4 illustrates an isometric rear view of the helmet of FIG. 3 in accordance with one embodiment.

Referring now to FIG. 4, a rear isometric view of the helmet 302 is illustrated. In the illustrated embodiment, the electronics compartment 364 is located at the rear of the helmet 302. According to this embodiment, components included in the electronic apparatus 230 are located within the compartment 364. In one embodiment, each of the following components illustrated in FIG. 2 are located in the compartment: the power source 234; the processor 236; the memory 238; the HUD display interface 240; and the communication system 250. Other elements illustrated in FIG. 2 and included in the apparatus 230 can also be housed in the electronics compartment depending on the embodiment. Access to the electronics compartment 364 can be provided by cover plate that is removably attached to the helmet 364. According to some embodiments, the electronics compartment includes impact absorbing material that helps "harden" the electronics against damage that would otherwise be caused during normal use of the helmet 302.

Figure 5:
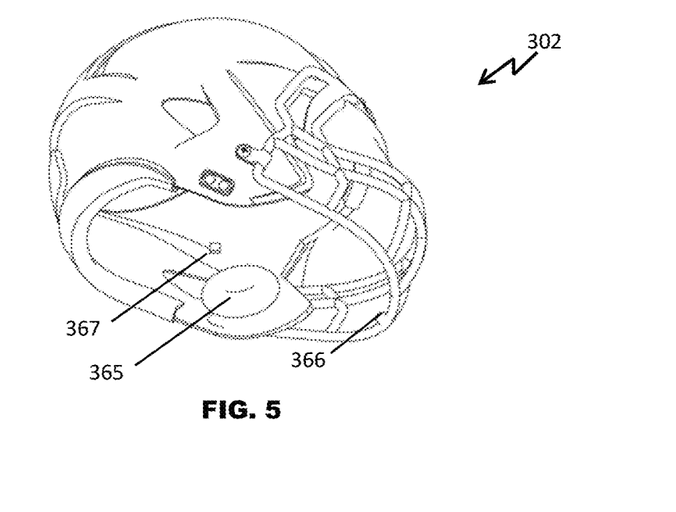
FIG. 5 illustrates an isometric view of an underside of the helmet of FIG. 3 in accordance with one embodiment.

Referring now to FIG. 5, elements of the communication system 250 and impact-detection system 242 are illustrated in accordance with one embodiment. According to this embodiment, the speaker 365 is located at an interior location in the helmet that is proximate to a location where the athlete's ear is located when the helmet 302 is worn. According to another embodiment, the speaker 365 includes a first speaker located proximate the athlete's left ear and a second speaker located proximate the athlete's right ear when the helmet 302 is worn. In general the speakers are employed to communicate audio information to the athlete. The audio information can include audio played along with corresponding video content. The audio can also include audio-only information communicated from coaches 108, medical staff 110 or in an automated way from the resources 106. For example, the audio can include an alert automatically generated at the resources 106 or an alert generated at the electronic device 230 housed in the helmet 302.

In addition, the helmet 302 and associated communication system includes the microphone 366. In the illustrated embodiment, the microphone is included as an integral part of the face mask so as to locate the microphone in proximity to the athlete's mouth when the helmet is worn. According to other embodiments, the microphone is secured to a different portion of the helmet. The microphone is used to communicate audio back to any of the resources 106, the coaches 108 and the medical staff 110.

According to some embodiments, the microphone 366 can be employed to improve practice efficiency by allowing communication between athletes during practice, to assist in a communication of play calls and to allow immediate and direct communication with medical and/or training staff 110. According to one embodiment, the communication system 250 is employed to perform testing in a concussion-protocol test for the athletes. In particular, the microphone can be employed with audio and or video received at the helmet 302 (for example, some form of Q&A) to assist in testing the athlete wearing the helmet for symptoms of a concussion.

Further, the audio provided by the athlete using the microphone 366 can be recorded for later review and/or medical audit.

In some embodiments, first inertial sensing system 367 is included in the impact-detection system 242. In the illustrated embodiment, the first inertial sensing system 367 is located adjacent the left side of the athlete's head when the helmet 302 is worn. Depending on the embodiment, the first inertial sensing system 367 can include one or more accelerometers, one or more gyroscopes or both as described above with reference to the electronic apparatus 230. Further, alternate locations or additional locations for the placement of inertial sensors can be used in various embodiments.

Figure 6:
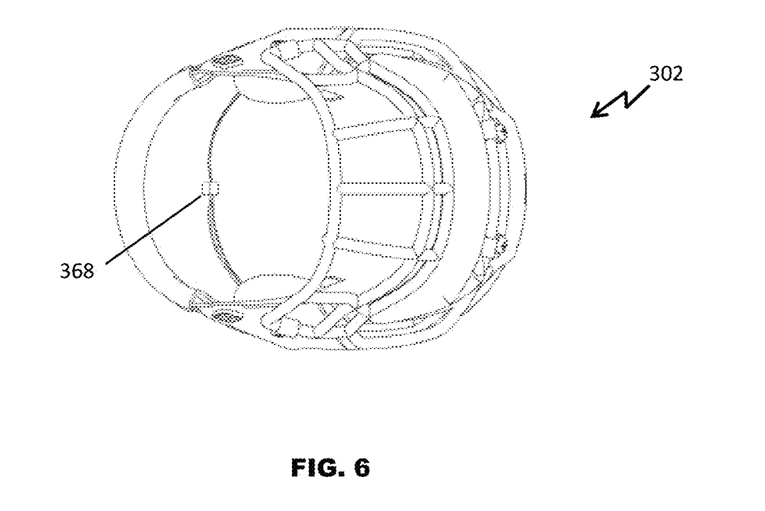
FIG. 6 illustrates a bottom view of the helmet of FIG. 3 in accordance with one embodiment.

Referring now to FIG. 6, a second inertial sensing system 368 is illustrated in accordance with one embodiment. In the illustrated embodiment, the second inertial sensing system 368 is located adjacent the rear of the athlete's head when the helmet 302 is worn. Depending on the embodiment, the second inertial sensing system 368 can include one or more accelerometers, one or more gyroscopes or both as described above with reference to the electronic apparatus 230.

Figure 7:
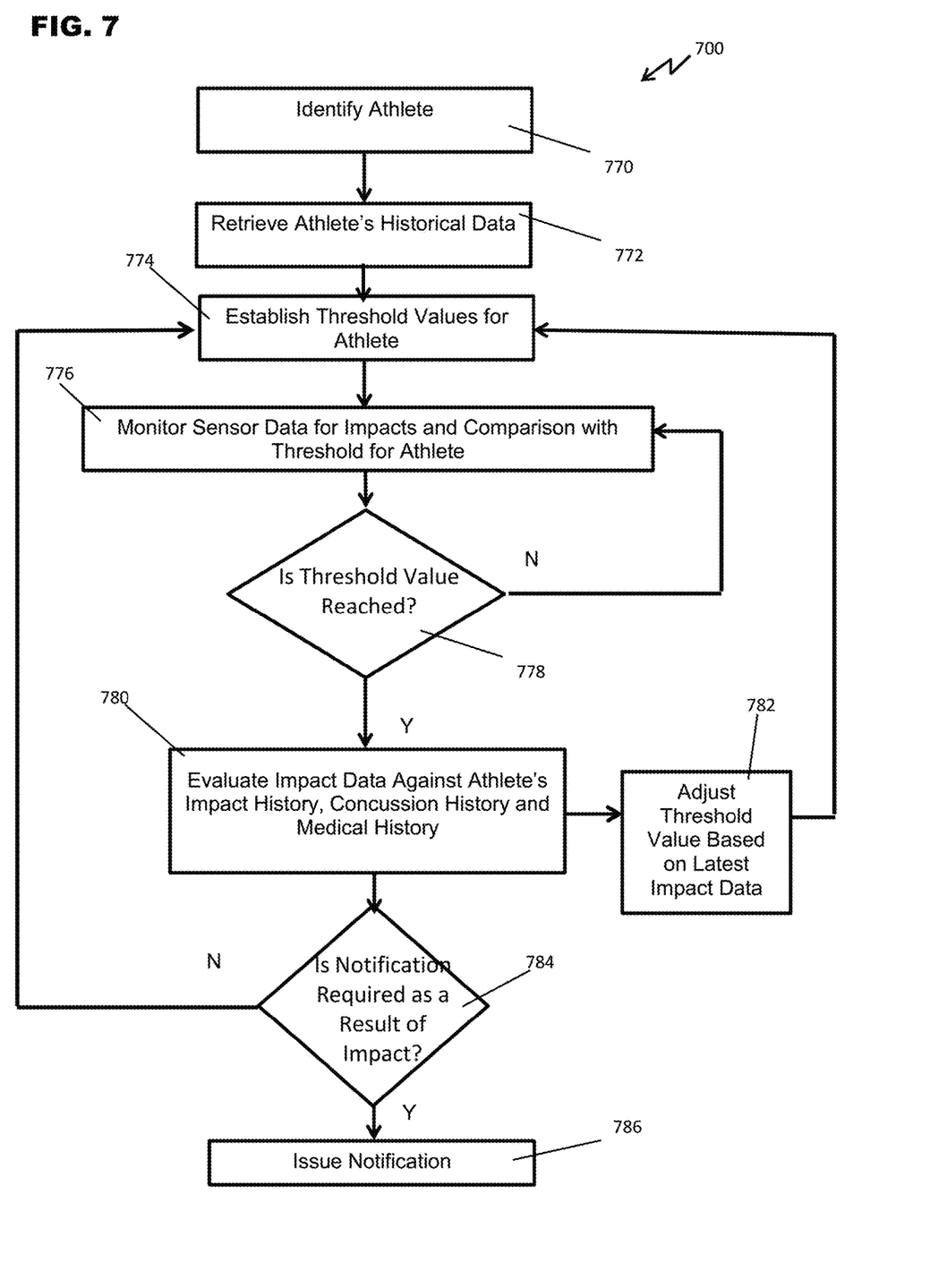
FIG. 7 illustrates a flow diagram of a process for impact analysis in accordance with one embodiment.

Referring now to FIG. 7, a process 700 for monitoring the well-being of an athlete is illustrated in accordance with one embodiment. In general, the process 700 is employed to reduce the risk that an athlete will suffer a concussion and/or to quickly detect a concussion to prevent further harm to the athlete. In some embodiments, the process 700 is employed to prevent an athlete from receiving a concussion. The preceding and other embodiments can employ historical information concerning an athlete in combination with data concerning impacts (for example, blows to the head) that are newly received due to the athlete's current participation in the sport. The historical data can be used to establish baseline values that are employed to assess the well-being of the athlete in view of newly-received impact data. The process 700 illustrates an overall approach in which sensor data concerning current impacts received by an athlete is evaluated against one or more threshold values to determine whether the impact is significant enough to warrant further evaluation. The further evaluation is used to determine whether the current impact data is meaningful to either or both of concussion prevention and concussion identification. The process includes the issuance of notifications when the current impact data does result in a meaningful change to actions associated with concussion prevention or concussion notification.

The process 700 includes a series of acts including actions and decision points. The actions include an act of identifying an athlete 770, an act of retrieving an athlete's historical data 772, an act of establishing threshold values for the athlete 774, an act of monitoring sensor data for the athlete 776, an act of evaluating impact data 780, an act of adjusting a threshold value for the athlete 782 and an act of issuing a notification 786. The decision points include an act of determining whether a threshold value is reached 782 and an act of determining whether a notification is required 784.

According to various embodiments, the system 100 and resources 106 can be employed to simultaneously monitor a plurality of athletes via the process 700. In these embodiments, the monitoring can be based on the impact data, concussion history and medical history specific to each of the athletes, respectively. In the illustrated embodiment, the process 700 begins with the act of identifying an athlete 770 that the system 100 is being employed to monitor. In one embodiment, the athlete activates the electronic system included in a selected one of the plurality of helmets 102A-C when they retrieve the helmet for use. For example, the athlete can activate the electronic apparatus 230 included in their helmet when they head out to the athletic field where they plan to participate in a practice or game. In a further embodiment, the electronic apparatus communicates a unique identifier associated with the athlete to the resources 106 via the network 104. In this embodiment, the process 700 operates thereafter until the athlete deactivates the electronic apparatus 230 included in their helmet. According to some embodiments, the coach 108 or member of the medical staff 110 receives information identifying each of their athletes participating in the practice or game. In these embodiments, the coach 108 or medical staff 110 can initiate the process 700 via one of the plurality of user devices 112.

The process continues at the act of retrieving an athlete's historical data 772. For example, the resources 106 can retrieve information for the athlete identified at the act 770. The information can include any one of the athlete's impact history, concussion history and medical history, any combination of the preceding or any one of or combination of the preceding in combination with other information. According to various embodiments, the information that is retrieved at the act 772 includes information maintained in one or more of the concussion history data storage 125, the medical history data storage 126 and the impact history data storage 128.

According to the illustrated embodiment, the process continues at the act of establishing threshold values 774 for the athlete. In general, the thresholds are set to determine the level at which sensor outputs may contribute to an identification of an athlete that has or may develop a concussion. That is, the process 700 can allow the system 100 to predict the likelihood that a concussion may result if the athlete's training or competitive activities are not modified. In some embodiments, the act of establishing the threshold values 774 is used to establish those impacts that are significant enough to warrant further evaluation for the athlete.

In some embodiments, the sensor data concerns one or more parameters known to relate to the likelihood that an athlete has or will suffer a concussion. For example, a threshold concerning a minimum impact-magnitude as measured by sensors included in the helmet 102 can be established. In practice, the threshold established for data measured by an inertial sensor located at a first location in the helmet 302 can differ from the threshold established for data measured by an inertial sensor located at a second location in the helmet. The preceding is useful where some points-of-impact are identified as being more closely associated with concussion-causing impacts than other point-of-impact. In this example, a parameter associated with impact-magnitude measured at a first location on the helmet is identified. A threshold for the corresponding inertial sensor measurement is then employed in the process 700.

As described in greater detail below, thresholds can also be customized on an athlete-by-athlete basis to address the athlete's risk of and/or propensity to being concussed. The customization can be made on an on-going basis to account for a cumulative effect of prior impacts, changes in the athlete's concussion history or changes in the athlete's medical history.

Thresholds can also be established for each of a magnitude of a newly-received impact, a location of a newly-received impact and a cumulative impact-value adjusted when a new impact is received by the athlete. In this example, a single threshold value can be established for each of the preceding parameters, or alternatively, multiple thresholds can be established for each of the preceding.

Further, while the act of establishing threshold values 774 refers to "thresholds" plural, the act 774 can be employed to establish a single threshold according to one embodiment. For example, an algorithm can employ a single threshold for sensor data that is established based on any one of or any combination of the athlete's impact history, concussion history and medical history, any combination of the preceding or any one of or combination of the preceding in combination with other information.

According to the illustrated embodiment, the process 700 continues at the act of monitoring sensor data 776, for example, monitoring data for impacts and comparison with the threshold values established for the athlete. In various embodiments, the data includes sensor data measured by the electronic apparatus 230 included in one of the plurality of helmets 102A-C. For example, the likelihood that an athlete will suffer a concussion may increase with repeated blows to the crown of the head. According to this embodiment, the data from an inertial sensing system located at the crown of the helmet has particular relevance. Data concerning the impacts detected by the sensors located at the crown of the helmet can be processed and compared with one or more related thresholds, for example, thresholds established at the act of establishing thresholds 776. The comparisons included in the act of monitoring sensor data 776 may be with a threshold established for a single current impact and/or a threshold established for cumulative impacts including the current impact. Where a threshold is established for cumulative impacts, the threshold can include a temporal element such that only sensor data for the more recent impacts is included in the cumulative total(s) that are processed.

The threshold values can be established for a plurality of parameters, for example, parameters that neurological professionals find most relevant for the prevention and/or detection of concussions. Data from different sensors included in the helmet 302 may have greater relevance to certain parameters, respectively. Thus, the acts of establishing thresholds and monitoring related senor data may address a plurality of parameters. Some examples of parameters include peak impact magnitudes measured by sensors, rates of acceleration, rates of deceleration, rates of angular rotation and peak angular displacement. Parameters may also be separately established for different directions of impact (for example, front impact, rear impact, side impact).

In addition, parameter selection and thresholds can be customized on an athlete-by-athlete basis, for example, where an athlete is found to be sensitive to a particular type of impact. As one example, an athlete's concussion history may identify the selected athlete as more concussion-prone than the norm. Consequently, the threshold values established at the act 774 may be lower for one athlete relative to other athletes. Further, in some embodiments, the act 776 is separated into two discrete acts: a first act that monitors and records sensor data; and a second act that compares the measured sensor data with the thresholds established at the act 774.

In the illustrated embodiment, the process 700 continues at the act of determining whether a threshold value is reached 778 for the parameter(s) as established at the act 774. Here, the comparison is completed for each of the parameters based on the values determined using sensor data for the current impact. According to some embodiments, the act of determining whether a threshold is reached operates to screen out data that does not make any significant contribution to evaluating whether an athlete's participation should be modified or stopped to either prevent an occurrence of a concussion or because the athlete has just suffered a concussion. For example, the act of determining whether a threshold is reached can eliminate the further processing of a low magnitude impact detected by the electronic apparatus 230.

According to the illustrated embodiment, if a threshold value is not reached, the process 700 returns to the act of monitoring sensor data 776. If a threshold value is reached, the process 700 moves to the act of evaluating impact data 780 against the athlete's impact history, concussion history and medical history. Often, the likelihood that an athlete may suffer a concussion in the future or is currently experiencing a concussion is dependent on information concerning an athlete's impact history, concussion history and medical history in addition to data for the current impact. For example, where impact data is relevant to an early warning parameter (i.e., an early indicator that an athlete is at a heightened risk of suffering a concussion), current impact data can be evaluated to determine whether the current impact in combination with any of the athlete's impact history, concussion history and medical history indicates that the risk of concussion is further heightened.

Optionally, the process 700 can also include the act of adjusting the threshold value 782, for example, based on the current impact data. In the illustrated embodiment, the act of adjusting the threshold value occurs following the act of evaluating impact data 780. Where the act 782 is included in the process 774, threshold values established for one or a plurality of parameters, respectively, can be adjusted. In one embodiment, the sensor data for the current impact can be combined with historical impact data from the same sensor to increase a measure of the cumulative impacts suffered by the athlete for a given period of time. The period of time can include, for example: the time since the start of a current practice or game (cumulative impacts in an event); the past 24 hours, a number of days, weeks or the time since a recovery from an earlier concussion. In this example, a relatively low level impact may become important because of the possible cumulative effect of impacts over time. For example, an impact that may previously been too low to be of interest, below previous thresholds for the parameter, may increase in importance such that a lower threshold is set.

The process 700 moves from the act 780 to the act of determining whether a notification is required 784. For example, the impact data can include a magnitude of a blow to the head as detected by an inertial sensing system included in the helmet 102. Where it is determined that the current impact alone or in combination with any of the athlete's impact history, concussion history and medical history increases the likelihood that the athlete has or will experience a concussion, a notification may be made to alert any of the athlete, the coach 108 and/or the medical staff 110. If a notification is required, the process 700 moves to the act of issuing a notification 786. Alternatively, if a notification is not required, the process 700 returns to the act of establishing threshold values 774 for further continued monitoring of the athlete's well-being.

The act of determining whether a notification is required 784 can include an act of determining the nature and type of notification. According to one embodiment, multiple threshold values are established at the act 774 and employed in the process 700. As one example, a first threshold can be established to provide a caution notification concerning the well-being of the athlete. In this example, a second threshold can be established to provide a "red-flag" warning that requires an immediate end to the athlete's participation in the practice or game.

Thus, the act of determining whether a notification is required 784 can include determining the relative importance of the notification, for example, "caution," "warning," "stop participation," "immediate medical attention required," etc. The act of determining whether a notification is required 784 can also include whether the notification is communicated via audio, video or other graphic representation, such as a blinking icon displayed in the heads up display or display screen included in selected ones of the plurality of user devices 112. According to another approach, coaches and/or medical staff can be provided with a graphics element representing each of the plurality of athletes equipped with one of the plurality of helmets 102A-C, respectively. In this embodiment, the characteristics of the graphics element can change when a notification issues concerning a selected athlete. For example, the graphics element can begin blinking to notify the coaching or medical staff of a change in the well-being of the athlete. The graphics element may also change color to make the staff aware of the change in status as determined by the system 100.

In one embodiment, the act of issuing the notification 786 includes determining the recipients of the message and the communication medium that is employed to provide the notification. According to one embodiment, the notification is issued via a local network, for example, Wi-Fi. The preceding can be effective where the resources 106, the plurality of helmets 102A-C, the coach 108 and the medical staff 110 are proximate to one another. In other embodiments, the communication includes the use of cellular data transmission, for example, where the notification is issued from resources 106 located remotely relative to the athlete and staff. According to still another embodiment, the notification is communicated from the resources 106 to the user device 112 in possession of the coach 108. The notification is then further communicated from the user device to either or both of the helmet 102 worn by the athlete and the medical staff 110. In one embodiment, the further communication is performed automatically. In another embodiment, the coach 108 must respond to the notification received by the user device 112 to push the notification to the athlete and staff 110.

As mentioned above, in various embodiments, the process 700 is employed with a plurality of athletes in a similar manner. That is, the resources 106 operate to maintain concussion history data, medical history data, impact history data and sensor data for a plurality of athletes. For example, each athlete may have a dedicated helmet 102 such that sensor data received from the helmet is uniquely associated with the athlete. Customized thresholds can be established based on the records personal to the athlete and a process corresponding to the process 700 can be separately established for each of the respective athletes.

In various embodiments, machine learning is employed to increase the effectiveness of the process 700. For example, a first set of data can be used to train the system 100 regarding the appropriate thresholds for given situations and conclusions reached concerning the proper issuance of notifications. The data set can include sensor data including measured data from sensors located at various locations in the helmet 102. The data set can also include information concerning any of the impact history, concussion history and medical history for athletes. The medical history can include outcomes such as occurrences when an athlete was identified as having received a concussion. The data set can further include information concerning any of an athlete's hydration level, body temperature, heart rate (including feedback indicative of a possible arrhythmia) and oxygen levels and/or oxygen intake for the athletes. Other physiological data or health-related information can be employed alone or in combination with the preceding in a machine learning process depending on the embodiment. The data set associated with the outcomes provides the examples used to train the system. For example, the data set can include a first subset used to establish initial parameter thresholds and a second subset which tests the system with human oversight to make adjustments to improve accuracy. Thereafter, the system can independently process information and draw conclusions concerning the well-being of the athlete, for example, whether the athlete has a heightened risk of receiving a concussion or has a concussion. In various embodiments, the data set includes data from a large number of different athletes in the selected sport. According to other embodiments, the data set includes data from a large number of different athletes from a plurality of different sports.

In some embodiments, an artificial intelligence machine-learning algorithm is trained using a supervised learning process. According to these embodiments, the training is preformed using an approach selected from a group consisting of: a decision tree methodology; a Naïve Bayes Classification; Least Squares Regression analysis; Logistic Regression analysis and a binary classification algorithm such as a support vector machine. Machine learning algorithms other than those listed here can be employed depending on the embodiment.

In various embodiments, the HUD 362 included in the helmets 102 provides for a visual and interactive information display to assist the athlete, the coach 108 and the medical staff 110. In addition to the notifications described above, this includes the display of practice footage, game footage, playbook review and data analytics to the athlete when the helmet is worn. The system also includes applications operating on the plurality of user devices 112. For the coach 108, the application allows a review of real-time practice footage that can include video from both on-board cameras 360 and cameras located at the athletic facility. The application can also allow the coach to annotate the video footage and share it with the athlete and other coaches. Content can also be forward to athletes, other coaches and medical staff via email. Further, the video recordings can be controlled and converted such that the footage is played back with different effects, for example, speeding up, slowing down (i.e., slow-motion) or pausing play back such as pausing playback in real time. Coaches 108 can employ user devices 112 to review video received from the plurality of helmets 102, to modify the footage and then communicate the revised video back to athletes wearing one of the plurality of helmets, respectively. All of the preceding can be employed to improve practice efficiency.

For the medical staff, an application operating on the plurality of user devices 112 can allow for live monitoring of on-field impacts to monitor athlete safety. The medical staff can also access the trained artificial intelligence based system to evaluate real-time impacts in view of the athlete's impact history, concussion history and medical history. The application can also allow medical and coaching staff to immediately access the athlete's impact history, concussion history and medical history.

According to some embodiments, the helmet-based safety system can employ augmented reality to improve safety and/or user performance. For example, an athlete can receive feedback that displays their technique alongside improved technique designed to reduce the risk of a concussion. Augmented reality can also be employed in reviewing playback of prior plays, to illustrate instructions concerning a play, to provide an interactive approach to an athlete's learning the playbook, to provide instructions on where to find information for a given play (including locating previously recorded video footage), to highlight athletes' of interest, to highlight a location of the ball during a play and to simulate different training environments. For example, augmented reality can be employed to demonstrate the importance of hand placement to an offensive lineman or a defensive lineman. According to this example, playback of an unsuccessful play or technique can include correct technique overlaid the actual technique in the video. In one embodiment, augmented reality can allow a coach to select a play that they would like their athletes to execute and then display the play on the HUDs included in the respective athletes' helmet. In this example, each athlete receives an overlaid track in their field of view that includes directions for their specific assignment for that play.

The impact detection and concussion monitoring described above is a result of the inclusion of sensors within a helmet worn by an athlete. However, in further embodiments, information from sensors located on the athlete or integrated in other elements of equipment worn by the athlete is also employed to assess the risk that an athlete may suffer a concussion or may have a concussion.

While the embodiments described herein are described with reference to football helmets, other embodiments are employed to protect athletes in other sports or activities where helmets or other headgear are worn, for example, hockey, lacrosse, bike riding, baseball and boxing. According to these embodiments, the system 100, resources 106, electronic apparatus 230 and process 700 described above can be employed with the helmet or headgear associated with the activity.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A system for use by athletes and their coaches during practice, the system comprising:
   a helmet-based electronic system including:
   a transparent display screen coupled to the helmet, the transparent display screen configured to display information to the user in a video format and a graphical format;
   a sensing system configured to sense a plurality of physiological states of the athlete when participating in a current practice-activity;
   a processor coupled to the transparent display screen and the sensing system, the processor configured to process information concerning the plurality of physiological states;
   and
   a first wireless transceiver coupled to the processor, the first wireless transceiver configured to communicate information concerning the plurality of physiological states,
   wherein a notification is automatically generated when a processing of the information concerning the plurality of physiological states results in a value that indicates that the athlete's physiological state is outside of recommended values when compared to at least one threshold concerning the plurality of physiological states, the notification displayed on the transparent display screen, the notification providing instructions for the athlete to modify the current practice-activity, and wherein the instructions indicate to the athlete that the current practice-activity should be shifted to a different practice-activity to provide a reduced level of physical exertion for the athlete.

2. The system of claim 1, wherein the processor is configured to determine the at least one threshold concerning the plurality of physiological states.

3. The system of claim 1, wherein the helmet-based electronic system includes an artificial intelligence engine configured to determine the at least one threshold concerning the plurality of physiological states.

4. The system of claim 3, wherein the system includes remote resources in communication with the helmet-based electronic system, and wherein the artificial intelligence engine is included in the remote resources.

5. The system of claim 3, wherein system includes at least one handheld processing device, wherein the system includes remote resources in communication with the helmet-based electronic system and the at least one handheld processing device, and wherein the artificial intelligence engine is included in at least one of the helmet-based electronic system, the handheld processing device and the remote resources.

6. The system of claim 5, wherein the notification is communicated for a review by a member of a coaching staff in possession of the at least one handheld processing device.

7. The system of claim 6, wherein a selection of the different practice-activity is determined, at least in part, by a member of the coaching staff.

8. The system of claim 1, wherein the plurality of physiological states include at least one of the athlete's hydration level, the athlete's body temperature, the athlete's heart rate and the athlete's oxygen levels.

9. The system of claim 1, wherein the notification includes a display of at least one quantified value concerning a physiological state selected from the plurality of physiological states.

10. The system of claim 1, wherein the notification is a first notification, wherein the sensing system is configured to provide information concerning at least one neurological state of the athlete, wherein a second notification is generated when a processing of the information concerning the at least one neurological state of the athlete results in a value that exceeds the threshold, and wherein the second notification is communicated for display on the transparent display screen.

11. The system of claim 1, wherein the second notification is automatically generated when the processing of the information concerning the at least one neurological state of the athlete results in the value that exceeds the threshold.

12. The system of claim 1, wherein the sensing system includes at least one of an inertial measurement sensor, RFID hardware and a location sensing system.

13. A system for use by athletes and their coaches during practice, the system comprising:

a helmet-based electronic system including:

a transparent display screen coupled to the helmet, the transparent display screen configured to display information to the user in a video format and a graphical format;

a sensing system configured to sense a plurality of physiological states of the athlete when participating in a current practice-activity;

a processor coupled to the transparent display screen and the sensing system, the processor configured to process information concerning the plurality of physiological states;

and a first wireless transceiver coupled to the processor, the first wireless transceiver configured to communicate information concerning the plurality of physiological states, wherein a notification is generated when a processing of the information concerning the plurality of physiological states results in a value that indicates that the athlete's physiological state is outside of recommended values when compared to at least one threshold concerning the plurality of physiological states, the notification displayed on the transparent display screen, the notification providing instructions for the athlete to modify the current practice-activity, and wherein the instructions indicate to the athlete that the current practice-activity should be shifted to a different practice-activity to provide a reduced level of physical exertion for the athlete.

14. The system of claim 13, wherein the processor is configured to determine the at least one threshold concerning the plurality of physiological states.

15. The system of claim 13, wherein the helmet-based electronic system includes an artificial intelligence engine configured to determine the at least one threshold concerning the plurality of physiological states.

16. The system of claim 15, wherein the system includes remote resources in communication with the helmet-based electronic system, and wherein the artificial intelligence engine is included in the remote resources.

17. The system of claim 15, wherein system includes at least one handheld processing device, wherein the system includes remote resources in communication with the helmet-based electronic system and the at least one handheld processing device, and wherein the artificial intelligence engine is included in at least one of the helmet-based electronic system, the handheld processing device and the remote resources.

18. The system of claim 17, wherein the notification is communicated for a review by a member of a coaching staff in possession of the at least one handheld processing device.

19. The system of claim 18, wherein a selection of the different practice-activity is determined, at least in part, by a member of the coaching staff.

20. The system of claim 13, wherein the plurality of physiological states include at least one of the athlete's hydration level, the athlete's body temperature, the athlete's heart rate and the athlete's oxygen levels.

21. The system of claim 13, wherein the notification includes a display of at least one quantified value concerning a physiological state selected from the plurality of physiological states.

22. The system of claim 13, wherein the notification is a first notification,
- wherein the sensing system is configured to provide information concerning at least one neurological state of the athlete,
- wherein a second notification is generated when a processing of the information concerning the at least one neurological state of the athlete results in a value that exceeds the threshold, and
- wherein the second notification is communicated for display on the transparent display screen.

23. The system of claim 13, wherein the second notification is automatically generated when the processing of the information concerning the at least one neurological state of the athlete results in the value that exceeds the threshold.

24. The system of claim 13, wherein the sensing system includes at least one of an inertial measurement sensor, RFID hardware and a location sensing system.

\* \* \* \* \*